United States Patent [19]

Dardik

[11] Patent Number: 4,848,329
[45] Date of Patent: Jul. 18, 1989

[54] MUCOID ABSORBING DRESSING

[76] Inventor: Herbert Dardik, 270 Highwood Ave., Tenafly, N.J. 07670

[21] Appl. No.: 91,662
[22] Filed: Sep. 1, 1987
[51] Int. Cl.⁴ .............................................. A61L 15/00
[52] U.S. Cl. .................................... 128/156; 128/888
[58] Field of Search ................ 128/155, 156; 604/306

[56] References Cited

U.S. PATENT DOCUMENTS

| | | | |
|---|---|---|---|
| 2,233,209 | 2/1941 | Herzog | 128/156 |
| 2,579,403 | 12/1951 | Slomowitz et al. | 128/156 |
| 2,682,873 | 7/1954 | Evans et al. | 128/156 |
| 2,893,388 | 7/1959 | Ganz | 128/156 |
| 2,969,144 | 1/1961 | Zackheim | 128/155 |
| 2,992,644 | 7/1961 | Plantinga et al. | 128/156 |
| 3,089,488 | 5/1963 | Owens | 128/156 |
| 3,366,112 | 1/1968 | Antonik | 604/306 |
| 4,245,630 | 1/1981 | Lloyd et al. | 128/155 |
| 4,519,798 | 5/1985 | Dinius | 128/156 |
| 4,615,880 | 10/1986 | Loth et al. | 128/156 |

Primary Examiner—Robert A. Hafer
Assistant Examiner—Charles H. Sam
Attorney, Agent, or Firm—Rosen, Dainow & Jacobs

[57] ABSTRACT

A method of absorbing secretions from urostomies or other body openings and a disposable mucoid absorbing dressing having a quantity of liquid absorbing material contained therein for absorbing mucus secretions from urostomies or other body openings is disclosed.

13 Claims, 2 Drawing Sheets

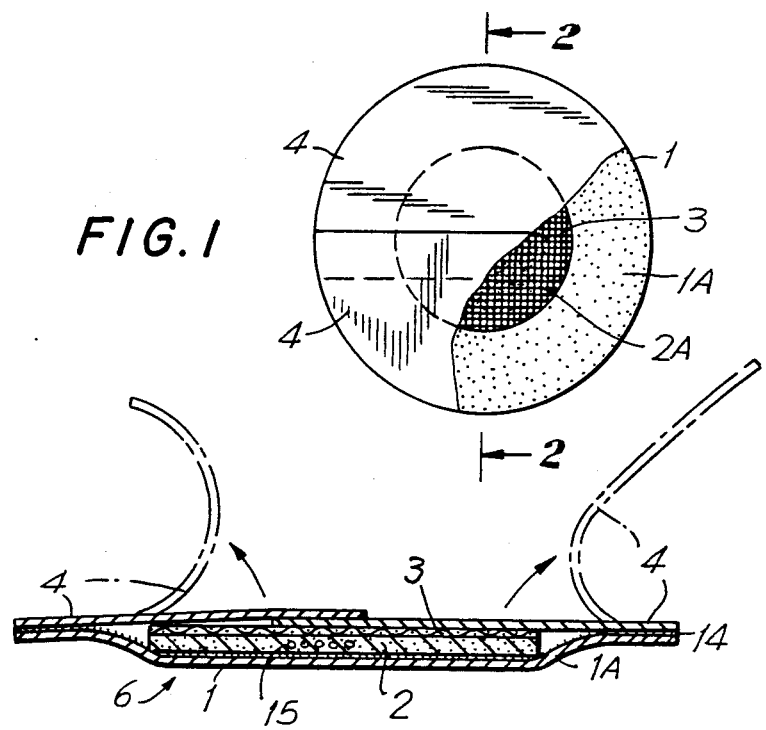
FIG. 1
FIG. 2
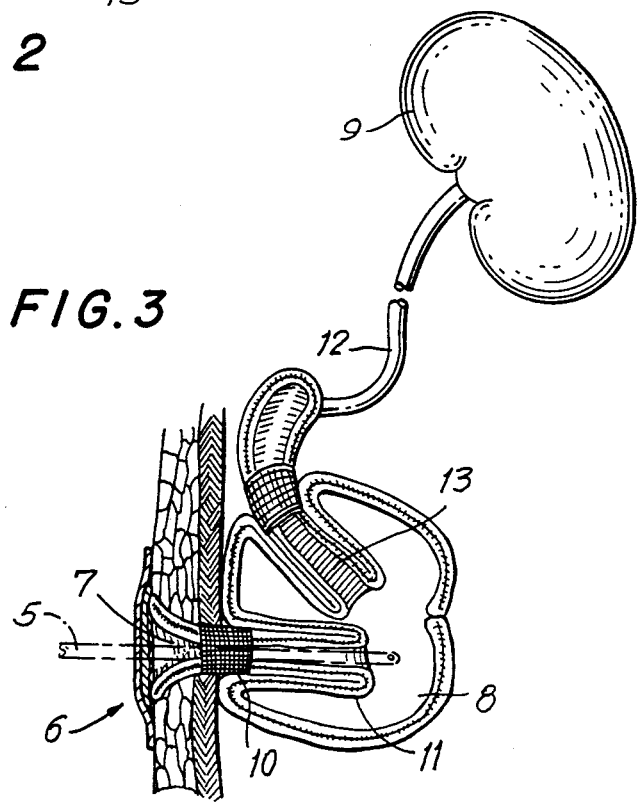
FIG. 3

MUCOID ABSORBING DRESSING

BACKGROUND OF THE INVENTION

This invention relates to a disposable mucoid absorbing dressing and particularly to a method of absorbing secretions from urostomies, the surgically formed artificial abdominal openings that serve as the exit sites for continent catheterizable ileal bladders or urinary reservoirs.

The terms "continent ileal bladders" or continent urinary reservoirs" refers to structures that collect and store urine and that are periodically emptied by catheterization of a cutaneous stoma or urostomy.

As is well known, the bladder is a membranous sac which serves as a receptacle for urine, which it receives through the ureters and discharges through the urethra. Disease or dysfunction of the urinary system has promted surgeons to replace or reconstruct the defective body part i.e. ureters, bladder and/or urethra, with expendable autologous tissue from the same or a different organ system. One such technique for the creation of a continent ileal bladder, called the Kock urinary reservoir, involves the construction of a urine storage component from a segment of the ileum, a part of the bowel. The afferent and efferent limbs of the bowel segment are intussuscepted or invaginated and supporting collars are fixed around the afferent inlet and the efferent outlet. Continence is achieved by means of the efferent ileal intussusception which protrudes into the urinary reservoir. The continence mechanism of the Kock urinary reservoir is similar to that of the normal urinary sphincter. That is, the resistance to urinary flow of the efferent ileal intussusception exceeds that of the intra-luminal pressures of the storage reservoir, thus preventing the involuntary voiding of urine. The afferent ileal intussusception operates in an identical manner as an antireflux mechanism, preventing backflow of urine from the reservoir into the ureters or drainage conduits.

A urostomy or opening fashioned in the abdominal wall serves as the entry site for the insertion of a catheter through the tight collar of the efferent ileal intussusception and into the urinary reservoir. While the catheter is in place drainage of urine proceeds. Both the tight collar around the outlet and the efferent ileal intussusception insure that urine is retained within the urinary reservoir except when the catheter is inserted.

Thus, the continent catheterizable ileal bladder is essentially "leak proof" as no large scale drainage of urine through the urostomy occurs except during catheterization. However, a certain amount of mucoid material or liquid body discharge may seep through the urostomy. Such seepage is both uncomfortable and unhygenic and may be embarrassing if wetness appears on clothing.

Applicant has discovered that application of the mucoid absorbing dressing of the present invention, having a quantity of liquid absorbing material contained therein, to the urostomy solves the problem of embarrassing mucoid seepage.

Accordingly, an object of this invention is to provide a method of absorbing mucus or liquid body discharge seeping from urostomies or other body openings.

A related object is to provide a method of absorbing mucus or liquid body discharge seeping from stomas that serve as the exit sites for continent catheterizable ileal bladders or urinary reservoirs.

A further object of this invention is to provide a mucoid absorbing dressing for contacting a person's body opening.

Still another object of this invention is to provide a mucoid absorbing dressing having a quantity of liquid absorbing material contained therein for absorbing mucus seeping from urostomies or other body openings.

SUMMARY OF THE INVENTION

According to the present invention, discomfort, irritation and embarrassment due to seepage of mucus or liquid body discharge from urostomies may be avoided. The continent ileal bladder patient can feel secure that mucoid seeping from his urostomy opening will not inadvertently wet or stain his clothing. The patient will also feel more comfortable, and the stoma will be more sanitary.

The present invention achieves the above-stated advantages in the following manner. The mucoid absorbing dressing of the present invention is applied directly over the urostomy opening. It is removed when the patient catheterizes himself or herself to drain the urine that has accumulated or when the mucoid absorbing dressing is saturated. Another mucoid absorbing dressing is then applied to insure personal hygiene and comfort.

The mucoid absorbing dressing for contacting a person's body opening comprises a quantity of liquid absorbing material; a pad having means for holding said quantity of liquid absorbing material distributed generally in a layer, said dressing having an inner absorbent layer for said contact with a body opening and an opposite outer layer; a backing sheet having an inner surface; a layer of adhesive on said inner surface and the backing sheet, said dressing adhering to said inner surface of the backing sheet; and a cover removably attached and covering the inner surface of said backing sheet of said pad.

Spherical hydrophilic beads of dextranomer sold under the trademark DEBRISAN ® is representative of the absorbent material which may be used. DEBRISAN ® beads, a product of Johnson & Johnson Corp. of New Brunswick, N.J. consists of spherical hydrophilic beads of dextranomer, 0.1–0.3 mm in diameter. The beads are composed of a three dimensional network of macromolecular chains of cross-linked dextran which is large enough to allow substances with a molecular weight of less than 1000 to enter freely. Substances with a molecular weight of 1000–5000 enter the beads less freely, while those with a molecular weight in excess of 5000 remain in the interspaces between the beads. Due to its hydrophilic properties, each gram of Debrisan beads can absorb approximately 4 ml. of fluid. The beads swell to approximately four times their original size. A quantity of 2 grams of DEBRISAN ® beads will be used.

DEBRISAN ® beads and DEBRISAN ® paste (3 parts DEBRISAN ® beads mixed with 1 part glycerin) have been used to remove exudates from the surface of wet ulcers or wounds. DEBRISAN ® have also been used to clean infected traumatic and surgical wounds and infected burns.

The mucoid absorbing dressing of the present invention adheres to the skin by means of a water impervious backing sheet with adhesive. The dressing is sealed by means of two overlapping sealing sheets which cover the entire package body and which adhere to the skin contacting means, such that the dressng can be exposed and applied to the skin surface by peeling back and removing the overlapping sealing sheets.

The mucoid absorbing dressing is protected from moisture and humidity by an external or outer package or bag. This external package bag is torn off and discarded when the mucoid absorbing dressing is ready to be used.

The present invention employs DEBRISAN ® beads to absorb mucoid or body fluid seepage from urostomies and other body openings. The mucus seeping from a urostomy which is the exit site for a continent catheterizable ileal bladder is typically not an infected fluid. It seeps out in minute amounts only. Note that the mucoid absorbing dressing of the present invention is not intended to replace catheterization to remove urine from the continent ileal bladder or urinary reservoir. The mucus or secretion absorbing dressng of the present invention is a convenient, hygenic mucoid absorbing treatment available to urostomy patients who have undergone continent ileal bladder surgery.

BRIEF DESCRIPTION OF THE DRAWINGS

For a fuller understanding of the invention, reference is made to the accompanying drawings:

FIG. 1 is a top plane view of the mucoid absorbing dressing with the sealing sheets partially broken away to reveal the backing sheet with adhesive and the pad.

FIG. 2 is a cross-sectional view of the mucoid absorbing dressing across lines 2—2 of FIG. 1.

FIG. 3 is a top plane view of the mucoid absorbing dressing covering a urostomy. The continent ileal bladder is also shown.

DESCRIPTION OF THE PREFERRED EMBODIMENTS

Figure 4:
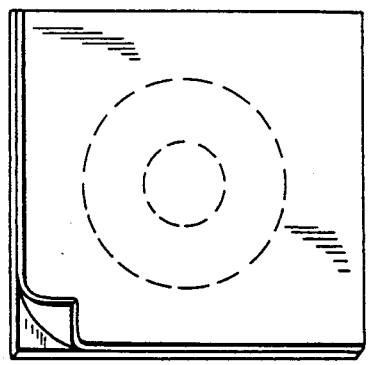
FIG. 4 is a top perspective view of the new dressing in a partially pealed-back sealed package.
Figure 5:
FIG. 5 is a cross-sectional view of a pad formed of inner and outer gauze layers with DEBRISAN ® beads between the layers.
Figure 6:
FIG. 6 is a cross-section of a pad formed of two outer gauze layers and two inner gauze layers with DEBRISAN ® beads between the double layers.
Figure 7:
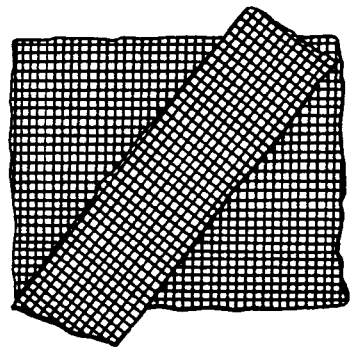
FIG. 7 is a fragmentary plane view of a pad showing one gauze layer positioned with its warp threads at an angle relative to the warp threads of the other gauze layer.
Figure 8:
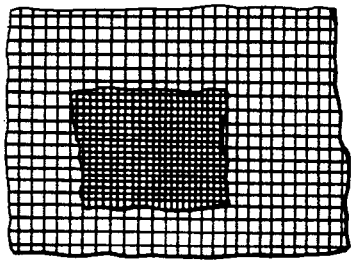
FIG. 8 is a fragmentary plan view of a pad showing one gauze layer with its warp threads laterally displaced from the warp threads of the other layer.
Figure 9:
FIG. 9 is a fragmentary sectional view of a pad formed of cotton between gauze layers with DEBRISAN ® beads in the cotton

FIG. 3 depicts a urostomy 7, the surgically formed artificial opening onto the abdominal surface that serves as the exit site for a continent catheterizable ileal bladder or urinary reservoir 8. The kidney 9, and the ureter or drainage conduit 12 leading from the kidney to the bladder, are also shown. Drainage or urine is accomplished when the patient removes the mucoid absorbing dressing 6 and inserts a drainage catheter 5 through the urostomy 7 and the collar 10 of the efferent ileal intussusception 11 into the continent ileal bladder 8. The afferent ileal intussusception 13 which acts as the antireflex mechanism of the continent ileal bladder is also shown. As indicated in FIG. 3, the disposable mucoid absorbing dressing of the present invention is adhered over the urostomy opening to absorb any mucus or fluid body discharge which should happen to seep out between catheterizations.

The mucoid absorbing dressing of the present invention is shown in FIGS. 1 and 2. The two overlapping sealing sheets 4 may be peeled back to open the mucoid absorbing dressing. A pad 2 having a quantity of DEBRISAN ® beads distributed generally in a layer 15 is shown with an inner layer of gauze 3 on its surface. As shown in FIGS. 1 and 2, the pad 2 has a smaller area than the backing sheet 1. Thus, backing sheet 1 has a surface area greater than that of the pad, thereby defining a donut-shaped margin area 1A with an exposed adhesive surface around pad 2. Accordingly, the pad's top surface 2A is exposed, and its bottom surface is adhered to the top surface of the backing sheet 1, with outer or margin areas of the backing sheet exposed. The dressing is applied to the urostomy surface by means of the backing sheet 1 with adhesive 14.

Mucoid absorbing material, sold under the tradename DEBRISAN ®, in the form of beads or paste, is distributed generally in a layer on the pad. This pad may be constructed in a variety of ways.

EXAMPLE 1

The pad may be constructed of gauze or other substantially porous fabric having substantial openings between the warp and weft threads. The pad may be constructed from a more tightly woven fabric as long as the flow of mucoid material through the fabric is not inhibited.

The pad may comprise two layers of gauze having mesh apertures smaller than 0.1 mm in diameter, an inner absorbent layer in contact with the skin surface and an opposite outer layer in contact with the backing sheet. Mucus absorbing material, sold under the tradename Debrisan is distributed generally between the two layers of gauze. The mesh apertures must be smaller than 0.1 mm to prevent the mucoid absorbing beads from falling out.

EXAMPLE II

In another version, the pad may comprise a plurality of inner gauze layers, i.e. two layers or a double layer and a plurality of outer gauze layers, with the mucoid absorbing material distributed generally in a layer between the inner and outer gauze layers.

Alternatively, the pad may comprise a plurality of gauze layers with mucoid absorbing material sold under the tradename DEBRISAN distributed generally between the various layers.

In either of these embodiments, the gauze layers must have mesh apertures smaller than 0.1 mm in diameter to prevent the mucoid absorbing beads sold under the tradename Debrisan from spilling out. Alternatively, the layers of gauze may have mesh apertures larger than 0.1 mm in diameter, so long as the gauze layers are oriented at different angles relative to each other or are oriented generally in the same direction, so that the warp threads in one layer of gauze lie parallel to the warp threads in the next layer of gauze but one thread is displace laterally from the other so that the warp threads are not one directly above the other. This construction presents a matrix of sufficiently small apertures transversely to prohibit DEBRISAN ® beads from falling out.

EXAMPLE III

In a preferred embodiment of this invention, the pad may be constructed of cotton sandwiched between an inner and an outer layer of gauze or layers of gauze. The cotton may be a single sheet or a plurality of sheets, with the mucoid absorbing beads or paste distributed generally in between the cotton fibers of the cotton sheet. An outer layer of gauze is preferred in this construction to prevent the cotton from clinging to the backing sheet with adhesive. The inner layer of gauze has mesh apertures sufficiently small to prevent Debrisan ® beads from falling out of the pad or is oriented as described above in Example II. This embodiment has the advantage of increased absorption capability, as both the cotton and the Debrisan ® beads act to absorb mucoid.

In any of the above described embodiments mucoid absorbing material sold under the tradename DEBRISAN ® may be used in any form. If DEBRISAN ® in paste form is used, it is layered on the pad at uniform concentration and distribution.

As noted supra, DEBRISAN ® beads measure 0.1-0.3 mm in diameter and may swell to approximately four times their original size upon absorption of fluid. The equation for the volume of a sphere is $V = 4/3 \, r^3$ where r is the radius of the bead. Accordingly, if $V_1$ = the original volume of a bead having radius $R_1$, and $V_2$ = the expanded volume of the bead four times greater than $V_1$, then the radius of the expanded bead is $$R_2 = R_1 \sqrt[3]{4.}$$

By this ratio, where $r_1 = 0.05$ mm, $r_2$ is 0.079 mm. This translates to an increase in bead diameter from 0.1 mm to 0.158 mm. Also, from the above equation, where $r_1$ is 0.15 mm, $r_2$ is 0.238 mm. Therefore the 0.3 mm bead will increase to 0.476 mm. It is clear that although the volume of the beads increases by a factor of approximately four, the diameter of the beads does not increase by the same amount. Therefore the pad as constructed in accordance with this invention is designed to accommodate the Debrisan ® beads even when they are saturated with mucus or body fluid.

It will be understood that the embodiments described above are merely exemplary and that persons skilled in the art may make many variations and modifications. Such variations are intended to be within the scope of the invention as set forth in the following claims.

What is claimed is:

1. A dressing for covering an opening on a person's body and absorbing fluid exudate therefrom, comprising:
    a pad having a top surface defining a first area and an opposite bottom surface,
    a water-impervious backing sheet having a top surface with an adhesive coating adjacent said bottom surface of the pad and adhered thereto, said backing sheet having area greater than said first area of said pad, whereby outer portions of said backing sheet extend beyond said area of the pad,
    a cover sheet overlying the top surface of said pad and overlying and removably adhered to said outer portions of said adhesive-coated backing sheet, said pad containing a layer of liquid-absorbing material comprising hydrophilic beads of dextranomer.

2. The dressing of claim 1 further comprising a readily openable sealed outer package containing said dressing and providing a humidity barrier therefore.

3. The dressing according to claim 1 wherein said pad comprises at least two layers of gauze, each having mesh apertures smaller than 0.1 mm in breadth, and said liquid-absorbing beads each having diameter of at least 0.1 mm and being disposed between said two layers of gauze.

4. A dressing according to claim 1 wherein said pad comprises at least two double layers of gauze, with said beads distributed as a layer between said two double layers, each double layer comprising at least two single layers of gauze.

5. A dressing according to claim 4 wherein each gauze layer comprises warp and weft threads, and wherein said warp threads of each single layer are oriented at an acute angle relative to the warp threads of the adjacent single layer.

6. A dressing according to claim 1 wherein said pad comprises at least two double layers of gauze, with said beads distributed as a layer between said two double layers, each double layer comprising at least two single layers, each single layer comprising sets of warp and weft threads, with the set of warp threads of one sngle layer oriented generally parallel to the set of warp threads of the other single layer and laterally displaced therefrom.

7. A dressing according to claim 1 wherein said pad comprises at least one layer of cotton comprising a plurality of cotton fibers sandwiched between two layers of gauze, and wherein said absorbent beads are distributed generally between said fibers.

8. A dressing according to claim 1 wherein said absorbent beads are spherical hydrophilic beads of dextranomer.

9. A dressing according to claim 8 wherein said absorbent material is a paste comprising 3 parts absorbent beads and 1 part glycerin.

10. A dressing according to claim 1 wherein each bead has the capacity to absorb approximately 4 ml of fluid and consequently swell to approximately 4 times its original size.

11. A dressing according to claim 1 wherein said cover sheet comprises a set of partially overlapping sheets which can be peeled back to uncover the top surface of said pad and said outer portions of said backing sheet.

12. The dressing of claim 1, wherein the liquid absorbing material comprises absorbent beads having a diameter in the range of 0.1 mm to 0.3 mm.

13. A method of absorbing mucus or liquid body discharge seeping from an urostomy that serves as the exit site for a continent catheterizable ideal bladder or other body opening comprising the steps of forming a dressing by providing a pad of at least two layers of fabric, the warp and weft threads of each layer of fabric defining apertures of a first diameter, distributing a quantity of liquid absorbing material comprising hydrophilic beads of dextranomer in a layer between said fabric layers, the beads having diameter greater than the diameter of said apertures in said fabric, thereby retaining said beads from falling out of the pad, providing a water-impervious outer layer having area greater than said pad and with adhesive on its inside surface, adhering said adhesive surface to the exposed outer surface of a first of said fabric layers with a marginal area of said adhesive coated surface exposed, placing said dressing with its second fabric adjacent the body opening and with said adhesive-coated marginal area of the outer layer adhered to the person's skin adjacent said opening.

* * * * *

UNITED STATES PATENT AND TRADEMARK OFFICE
CERTIFICATE OF CORRECTION

PATENT NO. : 4,848,329

DATED : July 18, 1989

INVENTOR(S) : H. Dardik

It is certified that error appears in the above-identified patent and that said Letters Patent is hereby corrected as shown below:

Column 2, line 36, change "and" to --of--.

Signed and Sealed this

Twenty-second Day of December, 1992

Attest:

DOUGLAS B. COMER

Attesting Officer

Acting Commissioner of Patents and Trademarks